(12) United States Patent
Shishika et al.

(10) Patent No.: US 9,105,453 B2
(45) Date of Patent: Aug. 11, 2015

(54) MASS SPECTROMETER AND MASS SPECTROMETRY

(71) Applicant: HITACHI HIGH-TECHNOLOGIES CORPORATION, Tokyo (JP)

(72) Inventors: Tsukasa Shishika, Tokyo (JP); Hidetoshi Morokuma, Tokyo (JP); Masuyoshi Yamada, Tokyo (JP); Hiroyuki Inoue, Kashiwa (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/396,228

(22) PCT Filed: Apr. 22, 2013

(86) PCT No.: PCT/JP2013/061732
§ 371 (c)(1),
(2) Date: Oct. 22, 2014

(87) PCT Pub. No.: WO2013/161737
PCT Pub. Date: Oct. 31, 2013

(65) Prior Publication Data
US 2015/0108341 A1    Apr. 23, 2015

(30) Foreign Application Priority Data
Apr. 23, 2012    (JP) .................................. 2012-097305

(51) Int. Cl.
*H01J 49/00*    (2006.01)
*B01D 59/44*    (2006.01)
(Continued)

(52) U.S. Cl.
CPC ............ *H01J 49/0022* (2013.01); *G06Q 10/20* (2013.01); *G08B 21/24* (2013.01); *H01J 49/025* (2013.01); *H01J 49/26* (2013.01)

(58) Field of Classification Search
USPC ............ 250/281–284, 288, 290–292, 339.07, 250/339.1–339.13, 340, 343, 379, 250/390.04–390.07, 526, 559.05–559.08; 356/72, 73, 256, 451, 456, 432–439, 356/441, 442
See application file for complete search history.

(56) References Cited

U.S. PATENT DOCUMENTS 6,468,748 B1 * 10/2002 Monforte et al. ............ 435/6.12
2003/0184733 A1 * 10/2003 Kameoka ........................ 356/73
(Continued)

FOREIGN PATENT DOCUMENTS

JP    10-106483 A    4/1998
JP    2003-294619 A    10/2003
(Continued)

OTHER PUBLICATIONS

International Searching Authority, International Search Report, Received in International Application No. PCT/JP2013/061732, mailed May 28, 2013.

*Primary Examiner* — Bernard E Souw
(74) *Attorney, Agent, or Firm* — Mattinly & Malur, PC

(57) ABSTRACT

A portable mass spectrometer that is carried to a sampling site to conduct analysis incorporates measures against erroneous operation. To prevent erroneous operation, when a measurement sample cannot be accurately analyzed because of contamination in the measurement sample, a criterion for aborting the sample measurement is provided and mass spectrometer control maintenance is performed. When urine is measured, the mass spectrometer detects the substances contained in the urine and automatically determines whether the sample is urine. The mass spectrometer then automatically selects an analysis condition specific to urine samples to make a measurement. Also with respect to sweat and saliva, the mass spectrometer similarly selects a specific analysis condition. The mass spectrometer automatically determines whether a sample, which is an internal standard sample contained in a sample case, is being measured on a measurement-by-measurement basis and automatically displays any error, interrupts the measurement, or carries out other processing.

17 Claims, 3 Drawing Sheets

(51) Int. Cl.
*B01D 59/50* (2006.01)
*G01N 21/00* (2006.01)
*H01J 49/26* (2006.01)
*H01J 49/02* (2006.01)
*G06Q 10/00* (2012.01)
*G08B 21/24* (2006.01)

(56) References Cited

U.S. PATENT DOCUMENTS

2005/0199801 A1 9/2005 Takada et al.
2006/0192101 A1 8/2006 Takada et al.
2007/0138384 A1* 6/2007 Keiser .......................... 250/282
2010/0134116 A1 6/2010 Ikeda et al.

FOREIGN PATENT DOCUMENTS

| JP | 2008-051520 A | 3/2008 |
| JP | 2009-518631 A | 5/2009 |
| WO | 02/25265 A1 | 3/2002 |
| WO | 2007/111110 A1 | 10/2007 |

* cited by examiner

MASS SPECTROMETER AND MASS SPECTROMETRY

TECHNICAL FIELD

The present invention relates to a portable mass spectrometer and a mass spectrometry suitable for sample measurement at a sampling point using a transportable or portable mass spectrometer.

BACKGROUND ART

In conjunction with the development of mass analytical instruments, the field of illegal drug analysis using a mass spectrometer has been developed. In actuality, mass spectrometers with gas chromatography are used in confirmative tests to confirm the usage of an illegal drug. However, it takes a relatively long time to analyze samples; therefore, this method is not suitable for continuous real-time monitoring of fluid samples or on-site drug determination.

For this reason, kits using an immunoassay method utilizing antigen-antibody reaction have come into use in on-site illegal drug investigations. As the result of actual use of an immunoassay method, it has been known that the method is high in sensitivity and selectivity to a specific drug. Meanwhile, when there are many drugs to be investigated, a plurality of types of kits are required according to the targets.

In conjunction with the development of micromachining technologies and the development of semiconductor technologies, mass spectrometers have been recently reduced in size and small-sized mass spectrometers have come into market. The appearance of these instruments makes it possible to carry the instruments to sample measurement sites.

With respect to conventional mass spectrometers, after taking a sample, the dedicated operator analyzes the sample in a chemical laboratory. It is determined by a dedicated operator whether an instrument is contaminated and which analysis conditions should be optimally selected for a drug to be measured. To make a measurement on site, it is critical to cope with fluctuation in environmental conditions, such as temperature and humidity, and any operating error that may be caused by someone other than the dedicated operator. Therefore, it is a challenge to realize a robust measurement and a measurement free from an operating error in the mass spectrometers.

In drug investigation or the like, it is required to measure the components of body fluids, such as urine, saliva, and sweat, to determine whether the drug is used. Also in these measurements, it is required to accurately identify a target substance among the components other than the target substance in a body fluid.

In connection with conventional technologies, Patent Literature 1 discloses a composite analyzer, easy to carry, obtained by combining a photometric analyzer and a mass spectrometer. The composite analyzer includes: a front end section that guides sample gas to be analyzed into the front end section and analyzes the gas by an opto-acoustic method; a photometric analyzer that guides the analyzed sample gas into the photometric analyzer and analyzes the sample gas by change in light passed through the sample gas; a mass spectrometer that guides the analyzed sample gas into the mass spectrometer and analyzes the mass of a sample gas component; a battery; and a carrying case for housing these items.

CITATION LIST

Patent Literature

PTL 1: Japanese Patent Application Laid-Open No. 2003-294619

SUMMARY OF INVENTION

Technical Problem

To carry a portable or transportable mass spectrometer to a sampling site to analyze a sample, it is important to obtain an accurate determination result. Especially, to use the mass spectrometer on an investigation site or the like, it is required to give maximum consideration to prevent the mass spectrometer from outputting an erroneous determination result. For this purpose, it is required to incorporate some measure against the erroneous operation into the mass spectrometer.

A first possible erroneous operation is a case where analysis conditions must be varied from sample to sample to be measured but analysis conditions are erroneously not varied. Especially, when a drug or the like is to be controlled, it may be required to vary analysis conditions (heating temperature or the like) between a body fluid sample and a solid illegal drug. It is required to realize such a mass spectrometer that, when a operator makes such a complicated determination, an operating error is prevented so that the investigation will not be influenced.

To prevent an erroneous determination, when a measurement sample cannot be accurately analyzed due to contamination or the like of the measurement sample in the mass spectrometer: a criterion for preventing continuous sample measurement with the mass spectrometer must be provided and the maintenance of the mass spectrometer is carried out based on the criterion.

In actual investigation, the upper limit of the concentration of a measurement sample cannot be defined. For this reason, there is a high possibility that a sample with a high concentration is measured. In an actual mass spectrometer, there is a possibility of carryover and the maintenance of the mass spectrometer may be required after a high-concentration sample measurement. Also to perform maintenance, it is important to determine whether the mass spectrometer must be cleaned or the replacement of a part is necessary to keep the mass spectrometer sound.

Solution to Problem

The present invention is a mass spectrometer formed by enclosing the following items in a case: a mass analysis unit that analyzes a sample taken into the body of the mass spectrometer; a display section; a power source; and a control section that controls the mass analysis unit and visualizes a data analysis result and causes the display section to display the result. The mass spectrometer is further provided with: a sample state detection section that detects the state of a sample inserted into the mass spectrometer; a sample contamination detection section that detects the state of contamination in the sample; and an mass spectrometer maintenance determination section that determines whether the maintenance of the mass spectrometer is required.

In the mass spectrometer, the sample state detection section detects whether a sample is a substance in the components of a body fluid containing at least one of urine, sweat, and saliva or a solid substance.

In the mass spectrometer, the control section identifies the type of a body fluid by a mass spectrum detected at the mass analysis unit, selects a corresponding component analysis mode, and starts a measurement sequence.

In the mass spectrometer, a corresponding component analysis mode includes a mass analysis range, a mass analysis condition, and a parameter for a temperature sequence.

In the mass spectrometer, the mass spectrometer maintenance determination section determines whether the maintenance of the mass spectrometer is required based on the signal intensity of a sample detected by the mass analysis unit.

In the mass spectrometer, the mass spectrometer maintenance determination section requests the maintenance of the mass spectrometer to a user when at least one of the following is equal to or higher than a certain level of intensity: the background intensity of a detection signal and the signal intensity of a measurement object.

In the mass spectrometer, a request for the maintenance of the mass spectrometer is for a blank measurement using a blank sample that is a standard substance for inspecting the state of the mass spectrometer.

The mass spectrometer has a sample case sensor that detects a blank sample case for housing a blank sample and sends a signal indicating the presence or absence of the blank sample case to the control section.

In the mass spectrometer, the mass spectrometer maintenance determination section requests the cleaning of the mass spectrometer or the replacement of a part to a user.

A mass spectrometry uses a mass spectrometer including: a mass analysis unit that analyzes a sample taken into the body of the mass spectrometer; a display section; a power source; and a control section that controls the mass analysis unit, visualizes a data analysis result, and causes the display section to display the result. In the mass spectrometry, a mode transition determination step is carried out to determine to which mode, body fluid component analysis mode or solid analysis mode, the mode should be caused to transition according to the state of a sample. Further, in the mass spectrometry, a mass analysis is conducted in either the body fluid component analysis mode or the solid analysis mode.

In the mass spectrometry, the type of a body fluid is identified by a detected mass spectrum, a corresponding component analysis mode is selected, and a measurement sequence is started.

In the mass spectrometry, a corresponding component analysis mode includes a mass analysis range, a mass analysis condition, and a parameter for a temperature sequence.

In the mass spectrometry, whether the maintenance of the mass spectrometer is required is determined based on the signal intensity of a sample detected.

In the mass spectrometry, the maintenance of the mass spectrometer is requested to a user when at least one of the following is equal or higher than a certain level of intensity: the background intensity of a detection signal and the signal intensity of a measurement object.

In the mass spectrometry, the cleaning of the mass spectrometer or the replacement of a part is requested to a user at the time of the maintenance of the mass spectrometer.

Advantageous Effects of Invention

The present invention is provided with functions of determining the state of the performance of cleaning, the presence or absence of a body fluid, and the like for the prevention of operating error in a portable mass spectrometer. As a result, the present invention brings about the following advantageous effects: an analysis can be easily and quickly conducted regardless of the type of a sample and the occurrence of an operating error and a possibility of erroneous operation can be reduced by conducting a mass analysis.

DESCRIPTION OF EMBODIMENTS

Figure 1:
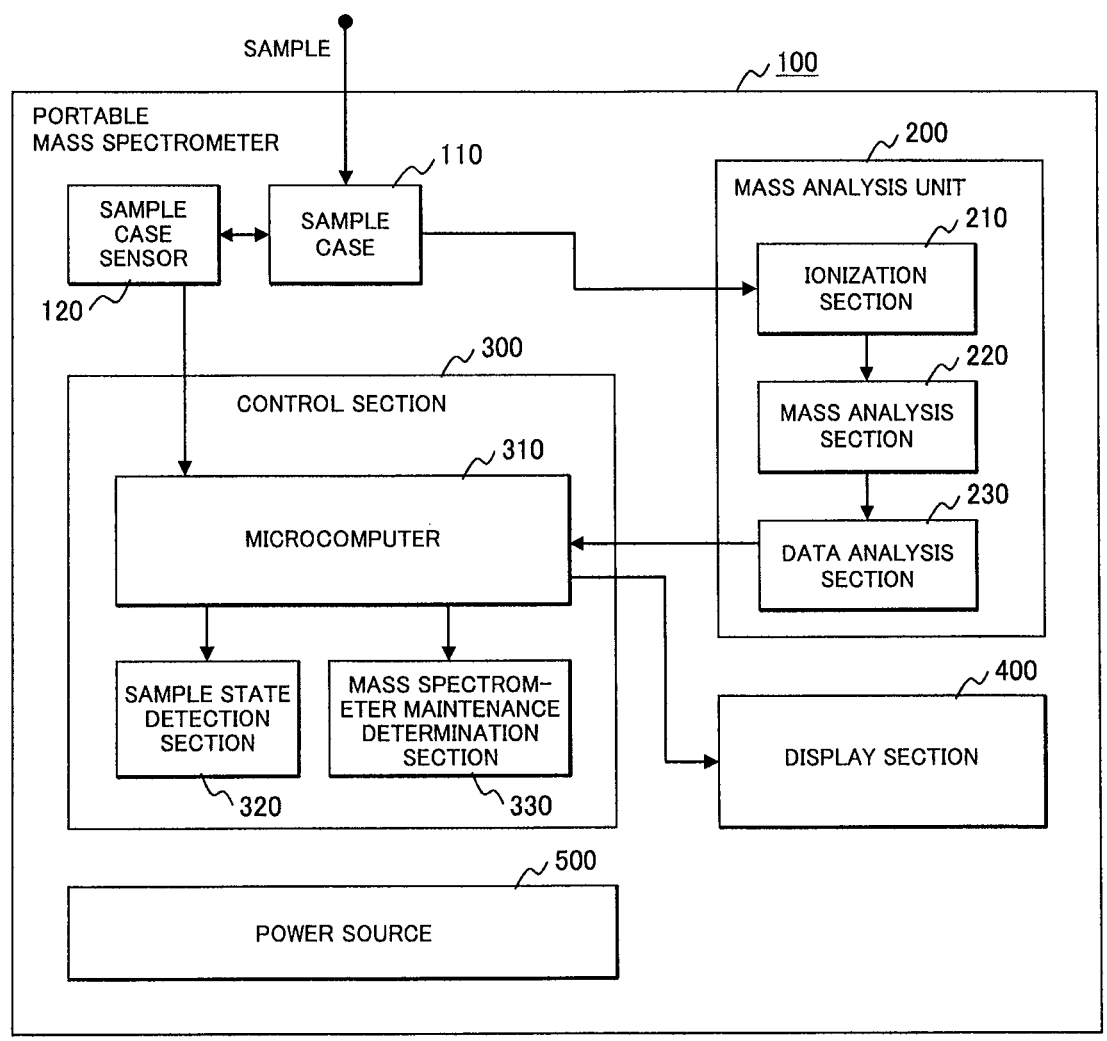
FIG. 1 is a block diagram illustrating the configuration of a mass spectrometer in an embodiment of the present invention.

A mass spectrometer embodying the present invention is used to make a sample measurement at a sampling point using a transportable or portable mass spectrometer.

When urine is taken as a measurement object, the mass spectrometer automatically detects a substance predominantly contained in the urine and automatically determines whether the object is urine by a mass analysis signal. When it is determined that the measurement object contains urine, the mass spectrometer automatically selects an analysis condition specific to the urine sample and makes a measurement. Also with respect to sweat, saliva, or the like, the mass spectrometer similarly uses a component predominantly contained in each body fluid as a selection criterion for a specific analysis condition.

When an ordinary sample is measured, a diluent containing an internal standard sample is added to a sample case on a measurement-by-measurement basis. It is automatically determined whether a sample containing the internal standard sample is being measured. The signal intensity and mass-to-charge ratio of a mass analysis output are calibrated according to the output of the internal standard sample. When a sample is an ordinary measurement sample, the control of error display, measurement interruption, and the like is automatically exercised.

With respect to mass spectrometer soundness check, the necessity for the maintenance of the mass spectrometer is determined each time a measurement is made. Specifically, the following measure is taken: a measured sample concentration is taken as a criterion; the maintenance of the mass spectrometer is warned of when either the integrated value of the output of measurement result or the integrated value within a specific range of the output exceeds the criterion. Thereafter, an ordinary mass analysis measurement is made.

When a warning has been outputted, it is requested to make a blank measurement for inspecting the state of the mass spectrometer at the next time of measurement. Whether a blank measurement has been made is determined based on the presence or absence of a standard sample in a blank sample. The blank sample cited here is a standard sample having a known output signal unlike ordinary measurement samples. The standard sample in the blank sample is a sample dedicated to blank measurements unlike internal standard samples for sensitivity and mass number calibration used in ordinary measurements. The blank sample is housed in, for example, a special case and it is checked by a sample case sensor whether a predetermined blank sample is loaded to the mass spectrometer.

When a blank measurement is not made, the mass spectrometer aborts the measurement and requests a blank measurement again. When at the time of completion of a blank measurement, the strength of a contaminant, such as a residual urine component or a residual drug (carryover), does not fall below a certain level, the mass spectrometer requests a blank measurement again. Or, the mass spectrometer requests the cleaning of the mass spectrometer or the replacement of a part. The determination of this request depends on the reduction ratio of the contaminant strength.

In FIG. 1, the portable mass spectrometer 100 is housed in a case, not shown, and includes: a sample case 110 for taking in a sample; a sample case sensor 120; a mass analysis unit 200 comprised of an ionization section 210 that ionizes the sample, a mass analysis section 220 that conducts a mass analysis, and a data analysis section 230 that analyzes an output result; a control section 300; a display section 400; and a power source 500 that supplies power to each constituent element of the mass spectrometer 100.

The control section 300 further includes a microcomputer 310, a sample state detection section 320, and an mass spectrometer maintenance determination section 330. The microcomputer 310 includes CPU, a memory, and control software dedicated to the mass spectrometer none of which is shown in the drawing. The microcomputer processes measurement information of the mass analysis unit 200 to visualize the information into a graph, characters, or the like and displays the visualized information on the display section 400.

In FIG. 1, the sample state detection section 320 and the mass spectrometer maintenance determination section 330 are depicted so that they are separated from the microcomputer 310. Instead, the sample state detection section 320 and the mass spectrometer maintenance determination section 330 may be configured as internal structures of the microcomputer 310.

<First Embodiment>

Figure 2:
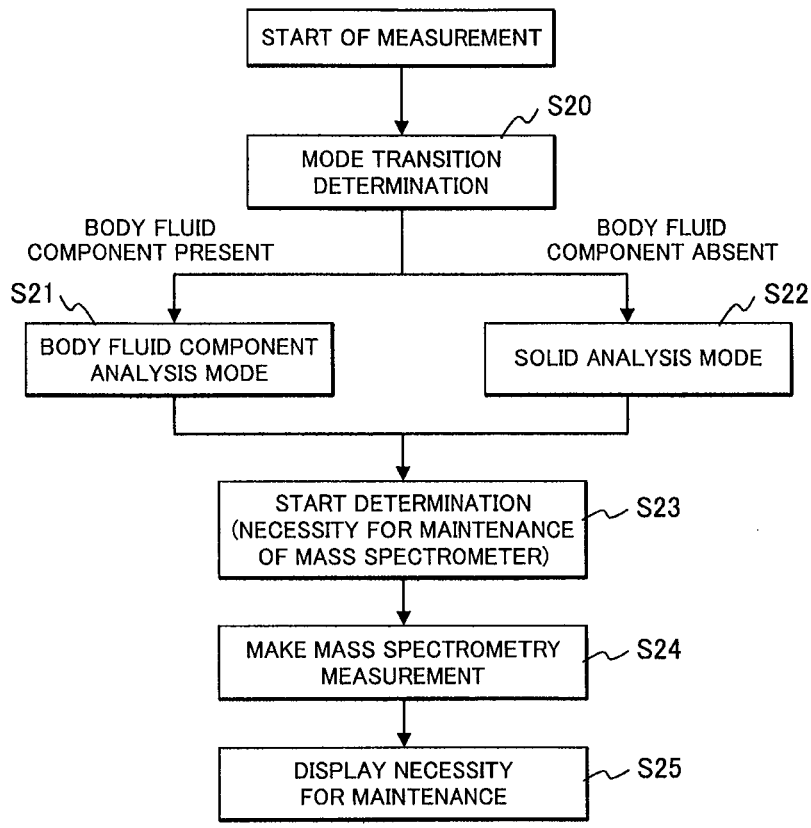
FIG. 2 is a flowchart illustrating an spectrometry for a mass spectrometer in an embodiment of the present invention.

In a first embodiment of the present invention in which urine is used as a body fluid, the body fluid determination method shown in FIG. 2 is carried out.

As illustrated by the flowchart shown in FIG. 2, at S20, the following processing is carried out after starting a measurement of the sample with the mass spectrometer 100: a mode transition determination is made at the control section 300 according to the state of the sample detected by the sample state detection section 320. When there is a body fluid component in the sample, the body fluid component analysis mode of S21 is selected and the measurement is advanced under various measurement conditions specific to the body fluid component. When there is not a body fluid component in the sample, the solid analysis mode of S22 is selected and the measurement is advanced under various measurement conditions specific to the solid samples.

At S23, subsequently, a determination of whether the maintenance of the mass spectrometer is required is started at the mass spectrometer maintenance determination section 330 of the control section 300 prior to a sample measurement.

At S24, subsequently, a mass analysis measurement is made.

When at S23, the above-mentioned predetermined conditions are met, at S25, the necessity for maintenance is displayed by the display section 400. When maintenance is unnecessary, the ordinary sample measurement process is advanced.

In the body fluid determination method, it is checked whether urine is contained in the sample and whether an intrinsic component (e.g. creatinine) contained in urine appears on a mass spectrum.

Figure 3:
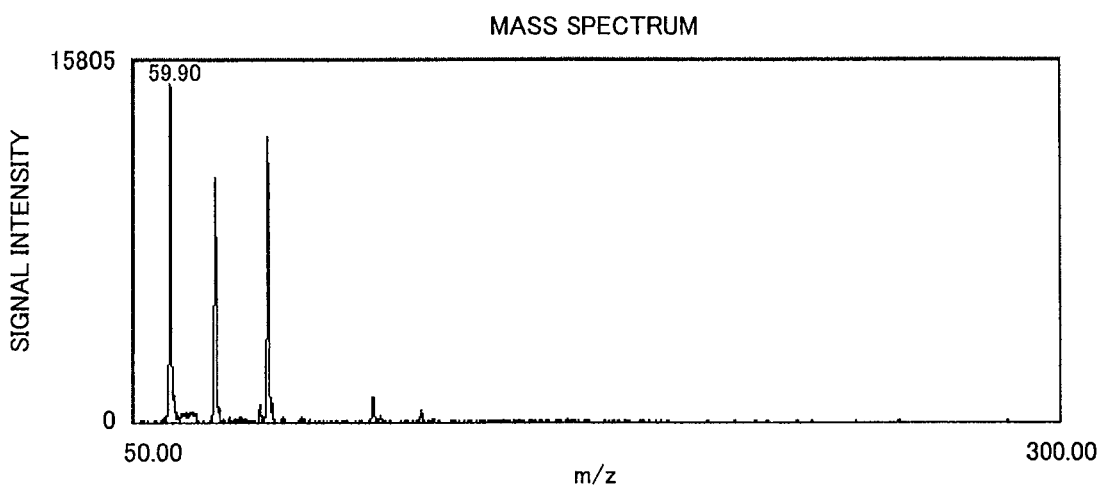
FIG. 3 is a graph showing a urine spectrum by a mass spectrometer in an embodiment of the present invention.

FIG. 3 is an example of a graph indicating a mass spectrum of a urine component in various body fluids. In the graph, the horizontal axis is taken for mass-to-charge ratio m/z and the vertical axis is taken for signal intensity. In the example in FIG. 3, a determination can be made using three peaks specific to the urine component as a marker with urine taken as a body fluid. Also when saliva or sweat is analyzed as a body fluid, a spectrum specific to each body fluid is similarly obtained and the type of the body fluid can be thereby determined.

At the stage where the components contained in urine are confirmed, the control section 300 of the portable mass spectrometer 100 selects an analysis mode for components including a body fluid and starts a measurement sequence. These component analysis modes include a mass analysis range, a mass analysis condition, and a parameter for a temperature sequence.

The temperature sequence parameter most largely differs depending on whether a body fluid is present. When a body fluid is present, a condition under which the body fluid will not bump is selected. When a body fluid is absent, the temperature is raised to the optimum temperature at which the components of the sample can be analyzed.

To make an accurate measurement, it is checked prior to transition to the actual measurement mode whether the maintenance of the mass spectrometer is required. To determine the necessity for the maintenance of the mass spectrometer, a determination is made based on: the background intensity of a detection signal; the signal intensity of the drug as the measurement object; and the signal intensity of components of the body fluid. When each item becomes equal to or higher than a certain level of intensity or the combined intensity of the individual items becomes equal to or higher than a certain level of intensity, the necessity for maintenance is notified to the user.

A description will be given to a determination method for checking whether the maintenance of the mass spectrometer is required with reference to the flowchart in FIG. 4. When mass spectrometer maintenance determination processing has not been completed after the measurement is started, the cleaning determination processing of S31 is carried out. When the blank sample is loaded to the mass spectrometer, at S32, the cleaning of the mass spectrometer is carried out and at S34, a determination is started with respect to the replacement of a part. When the carryover is equal to or less than a predetermined value, at S35, the cleaning is completed and at S36, the maintenance of the mass spectrometer is completed. When the blank sample is not loaded to the mass spectrometer, at S33, the display section 400 is caused to display an error and a remeasurement is requested.

Meanwhile, when the mass spectrometer maintenance processing has been completed, at S37, a mode transition determination is made. When there is a body fluid component, the body fluid component analysis mode of S38 is adopted and when there is not a body fluid component, the solid analysis mode of S39 is adopted. At S40, subsequently, a determination is started with respect to the necessity for cleaning. When cleaning or the like is required after a mass analysis measurement is made at S41, at S42, it is displayed that maintenance is required before the next measurement.

The user notified of the necessity for cleaning thereafter carries out the cleaning of the mass spectrometer.

To confirm whether cleaning has been carried out, a dedicated case is used in cleaning and for the dedicated case, a blank sample encapsulating a standard substance for checking cleaning is used. When cleaning is carried out, the cleaning is completed after the following are confirmed: that the intensity of each carryover component is equal to or less than a certain value and that the standard substance appears indicating a certain value or more.

When the completion conditions are not met, it is considered that the end of part life has come and the necessity for the replacement of a part is announced. After part replacement, cleaning is carried out again and a cleaning determination is made.

<Second Embodiment>

In the body fluid determination method in a second embodiment of the present invention, the following are checked: whether saliva is contained in the sample and whether a component contained in the saliva appears on a mass spectrum.

At the stage where the components contained in the saliva are confirmed, the control section 300 of the mass spectrometer 100 selects an analysis mode for components including a body fluid and starts a measurement sequence. These component analysis modes include a mass analysis range, a mass analysis condition, and a parameter for a temperature sequence.

Figure 4:
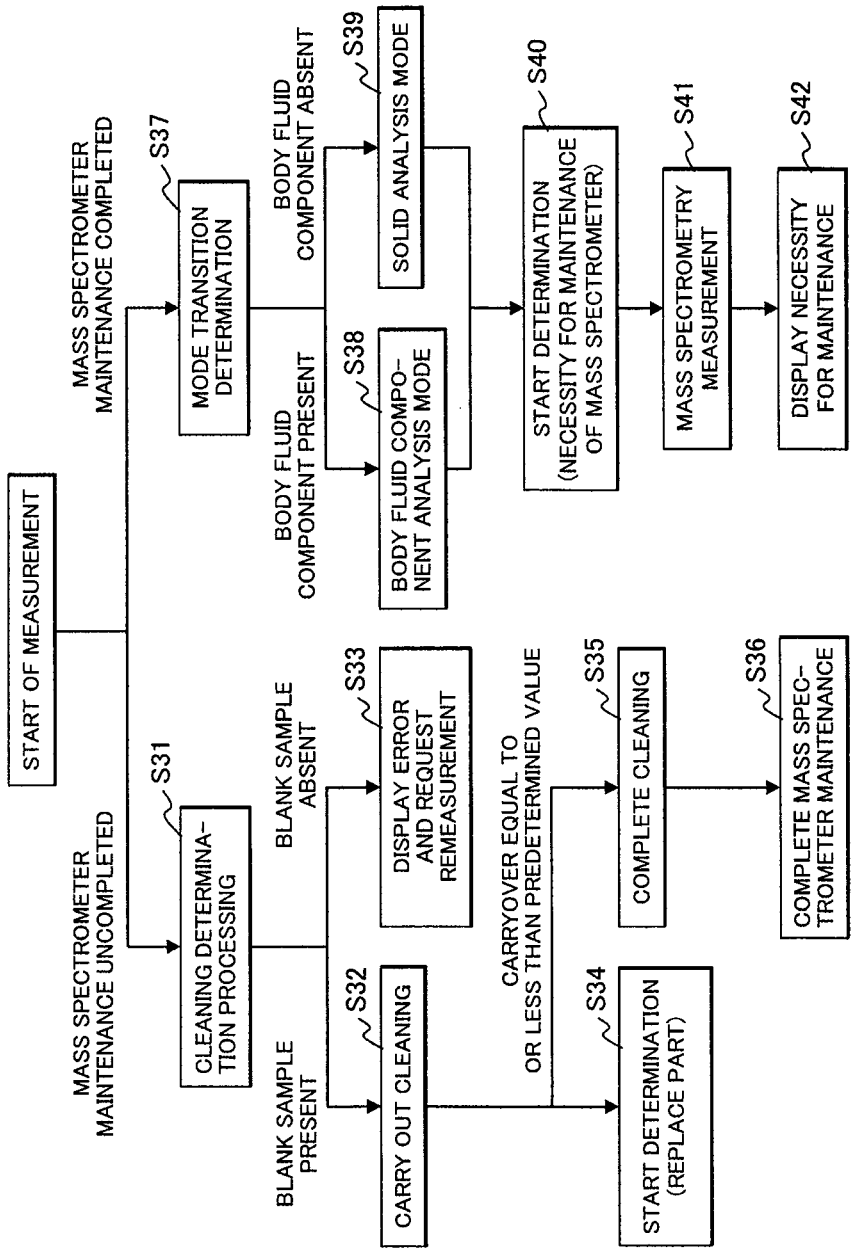
FIG. 4 is a flowchart illustrating an spectrometry for a mass spectrometer in an embodiment of the present invention.

The determination of the maintenance of the mass spectrometer shown in FIG. 2 and the determination method for the necessity for the replacement of a part and cleaning shown in FIG. 4 are the same as in the first embodiment.

<Third Embodiment>

In the body fluid determination method in a third embodiment of the present invention, the control section 300 of the mass spectrometer 100 checks the following: whether sweat is contained in the sample and whether the components (lactic acid and fatty acid) contained in the sweat appear on a mass spectrum. At the stage where the components contained in the sweat are confirmed, the mass spectrometer selects an analysis mode for components including a body fluid and starts a measurement sequence.

The determination of the maintenance of the mass spectrometer shown in FIG. 2 and the determination method for the necessity for the replacement of a part and cleaning shown in FIG. 4 are the same as in the first embodiment.

REFERENCE SIGNS LIST

100 . . . portable mass spectrometer,
110 . . . sample case,
120 . . . sample sensor,
200 . . . mass analysis unit,
210 . . . ionization section,
220 . . . mass analysis section,
230 . . . data analysis section,
300 . . . control section,
310 . . . microcomputer,
320 . . . sample state detection section,
330 . . . mass spectrometer maintenance determination section,
400 . . . display section,
500 . . . power source.

The invention claimed is:

1. A mass spectrometer formed by housing in a case a mass analysis unit that analyzes a sample taken into the body of the mass spectrometer, a display section, a power source, and a control section that controls the mass analysis unit, visualizes a data analysis result, and causes the display section to display the visualized result, the mass spectrometer comprising:
a sample state detection section that detects the state of a sample inserted into the mass spectrometer; a sample contamination detection section that detects the state of contamination in the sample; and an mass spectrometer maintenance determination section that determines the necessity for the maintenance of the mass spectrometer.

2. The mass spectrometer according to claim 1,
wherein the sample state detection section detects whether a sample is a substance in body fluid components including at least one of urine, sweat, and saliva or a solid substance.

3. The mass spectrometer according to claim 2,
wherein the control section identifies the type of a body fluid by a mass spectrum detected at the mass analysis unit and selects a corresponding component analysis mode and starts a measurement sequence.

4. The mass spectrometer according to claim 3,
wherein the corresponding component analysis mode includes a mass analysis range, a mass analysis condition, and a parameter for a temperature sequence.

5. The mass spectrometer according to claim 1,
wherein the mass spectrometer maintenance determination section determines the necessity for the maintenance of the mass spectrometer based on the signal intensity of a sample detected by the mass analysis unit.

6. The mass spectrometer according to claim 5,
wherein the mass spectrometer maintenance determination section requests the maintenance of the mass spectrometer to a user when at least one of the background intensity of a detection signal and the signal intensity of a measurement object is equal to or higher than a certain level of intensity.

7. The mass spectrometer according to claim 6,
wherein the request for the maintenance of the mass spectrometer is a request for a blank measurement using a blank sample that is a standard substance for inspecting the state of the mass spectrometer.

8. The mass spectrometer according to claim 7, comprising:
a sample case sensor that detects a blank sample case for housing the blank sample,
wherein a signal indicating the presence or absence of the blank sample case is sent to the control section.

9. The mass spectrometer according to claim 6,
wherein the mass spectrometer maintenance determination section requests the cleaning or the replacement of a part of the mass spectrometer to a user.

10. A mass spectrometry using a mass spectrometer including: a mass analysis unit that analyzes a sample taken into the body of the analysis; a display section; a power source; and a control section that controls the mass analysis unit, visualizes a data analysis result, and causes the display section to display the visualized result,
wherein a mode transition determination step in which the mode is caused to transition to either body fluid component analysis mode or solid analysis mode according to the state of a sample and a mass analysis in either the body fluid component analysis mode or the solid analysis mode are carried out.

11. The mass spectrometry according to claim 10,
wherein the type of a body fluid is identified by a detected mass spectrum, a corresponding component analysis mode is selected, and a measurement sequence is started.

12. The mass spectrometry according to claim 11,
wherein the corresponding component analysis mode includes a mass analysis range, a mass analysis condition, and a parameter for a temperature sequence.

13. The mass spectrometry according to claim 10,
wherein the necessity for the maintenance of the mass spectrometer is determined based on the signal intensity of a sample detected.

14. The mass spectrometry according to claim 13,
wherein the maintenance of the mass spectrometer is requested to a user when at least one of the background intensity of a detection signal and the signal intensity of a measurement object is equal to or higher than a certain level of intensity.

15. The mass spectrometry according to claim 14,
wherein at the time of the maintenance of the mass spectrometer, the cleaning or the replacement of a part of the mass spectrometer is requested to a user.

16. The mass spectrometer according to claim 7,
wherein the mass spectrometer maintenance determination section requests the cleaning or the replacement of a part of the mass spectrometer to a user.

17. The mass spectrometer according to claim 8,
wherein the mass spectrometer maintenance determination section requests the cleaning or the replacement of a part of the mass spectrometer to a user.

\* \* \* \* \*